(12) United States Patent
Thennati et al.

(10) Patent No.: US 10,085,961 B2
(45) Date of Patent: Oct. 2, 2018

(54) PHARMACEUTICAL COMPOSITIONS OF DIMETHYL FUMARATE

(71) Applicant: SUN PHARMACEUTICAL INDUSTRIES LIMITED, Mumbai, Maharashtra (IN)

(72) Inventors: Rajamannar Thennati, Baroda (IN); Shirish Kulkarni, Baroda (IN); Amol Kulkarni, Baroda (IN); Vimal Kaneria, Baroda (IN); Mukesh Sharma, Baroda (IN)

(73) Assignee: SUN PHARMACEUTICAL INDUSTRIES LIMITED, Mumbai, Maharashtra (IN)

( * ) Notice: Subject to any disclaimer, the term of this patent is extended or adjusted under 35 U.S.C. 154(b) by 0 days.

(21) Appl. No.: 15/170,421

(22) Filed: Jun. 1, 2016

(65) Prior Publication Data

US 2016/0346393 A1 Dec. 1, 2016

(30) Foreign Application Priority Data

Jun. 1, 2015 (IN) .......................... 2125/MUM/2015

(51) Int. Cl.
*A61K 9/48* (2006.01)
*A61K 31/225* (2006.01)

(52) U.S. Cl.
CPC .......... *A61K 31/225* (2013.01); *A61K 9/4808* (2013.01)

(58) Field of Classification Search
CPC ...... A61K 31/225; A61K 9/28; A61K 9/2806; A61K 9/4808
See application file for complete search history.

(56) References Cited

U.S. PATENT DOCUMENTS

| | | | |
|---|---|---|---|
| 6,509,376 B1 | 1/2003 | Joshi | |
| 6,858,750 B2 | 2/2005 | Joshi et al. | |
| 7,226,613 B2 * | 6/2007 | Schleifenbaum | A61J 3/07 424/440 |
| 7,320,999 B2 | 1/2008 | Joshi et al. | |
| 7,619,001 B2 | 11/2009 | Joshi et al. | |
| 7,803,840 B2 | 9/2010 | Joshi et al. | |
| 8,399,514 B2 | 3/2013 | Lukashev et al. | |
| 8,524,773 B2 * | 9/2013 | Joshi | A61K 9/1676 514/547 |
| 8,759,393 B2 | 6/2014 | Joshi et al. | |
| 8,906,420 B2 | 12/2014 | Nilsson et al. | |
| 9,326,947 B1 | 5/2016 | Dyakonov et al. | |
| 9,326,965 B2 | 5/2016 | Dyakonov et al. | |
| 9,422,226 B2 * | 8/2016 | Guzowski | C07C 67/08 |
| 2008/0299196 A1 | 12/2008 | Nilsson et al. | |
| 2009/0304790 A1 | 12/2009 | Nilsson et al. | |
| 2013/0259906 A1 | 10/2013 | Nilsson et al. | |
| 2014/0099364 A2 | 4/2014 | Nilsson et al. | |
| 2014/0142095 A1 * | 5/2014 | Cortopassi | A61K 31/225 514/224.8 |
| 2014/0284245 A1 | 9/2014 | Karaborni et al. | |
| 2014/0348915 A9 | 11/2014 | Karaborni et al. | |
| 2015/0024049 A1 | 1/2015 | Nilsson et al. | |
| 2015/0079180 A1 | 3/2015 | Karaborni et al. | |
| 2015/0209318 A1 | 7/2015 | Goldman et al. | |
| 2015/0272894 A1 | 10/2015 | Nilsson et al. | |
| 2016/0199335 A1 | 7/2016 | Dyakonov et al. | |
| 2016/0199336 A1 | 7/2016 | Dyakonov et al. | |
| 2016/0206586 A1 | 7/2016 | Galetzka et al. | |
| 2016/0206587 A1 | 7/2016 | Galetzka et al. | |

FOREIGN PATENT DOCUMENTS

| | | |
|---|---|---|
| WO | 2013076216 A1 | 5/2013 |
| WO | 2015028472 A1 | 3/2015 |
| WO | 2015028473 A1 | 3/2015 |
| WO | 2015086467 A1 | 6/2015 |
| WO | 2016081671 A1 | 5/2016 |
| WO | 2016081676 A1 | 5/2016 |
| WO | 2016090154 A1 | 6/2016 |
| WO | 2016113754 A2 | 7/2016 |

OTHER PUBLICATIONS

Ruggieri et al.; Pharmacology and clinical efficacy of dimethyl fumarate (BG-12) for treatment of relapsing-remitting multiple sclerosis; Therapeutics and Clinical Risk Management, 2014, 10, 229-239.

Antonie et al,; Use of fumaric acid esters in psoriasis; Indian Journal of Dermatology, Venereology and Leprology, vol. 73, No. 2, Mar.-Apr. 2007, pp. 133-137.

Phillips et al.; Managing flushing and gastrointestinal events associated with delayed-release dimethyl fumarate: Experiences of an international panel; Multiple Sclerosis and Related Disorders (2014) 3, 513-519.

Sheikh et al.; Tolerability and Pharmacokinetics of Delayed-Release Dimethyl Fumarate Administered With and Without Aspirin in Healthy Volunteers; Clinical Therapeutics, 2013, vol. 35, No. 10, 1583-1594.

Werdenberg et al.: Presystemic Metobolism and Intestinal Absorption of Antipsoriatic Fumaric Acid Esters, Biopharm. Drug Dispos. 2003, 24: 259-273.

* cited by examiner

*Primary Examiner* — Lakshmi S Channavajjala
(74) *Attorney, Agent, or Firm* — Sughrue Mion, PLLC

(57) ABSTRACT

The present invention relates to pharmaceutical compositions comprising dimethyl fumarate and a pharmaceutically acceptable agent which inhibits the enzyme catalyzed degradation of dimethyl fumarate.

10 Claims, No Drawings

PHARMACEUTICAL COMPOSITIONS OF DIMETHYL FUMARATE

FIELD OF THE INVENTION

The present invention relates to pharmaceutical compositions comprising dimethyl fumarate and a pharmaceutically acceptable agent which inhibits the enzyme catalyzed degradation of dimethyl fumarate.

BACKGROUND OF THE INVENTION

Fumaric acid esters have been used for the treatment of moderate to severe psoriasis. In 1994, mixture of fumaric acid esters like dimethyl fumarate ester and monoethyl fumarate was approved in Germany, for the treatment of psoriasis. The product was marketed under the tradename Fumaderm®. (Ruggieri et al, Therapeutics and Clinical Risk management, 2014, 10, 229-239). Fumaderm® is an enteric coated tablet comprising dimethyl fumarate, monoethylfumarate fumarate Ca-salt, monoethylfumarate fumarate Mg-salt and monoethylfumarate Zn-salt.

Fumaric acid and its derivatives like dimethyl fumarates was known to cause local irritation of the intestinal mucous membrane when administered as conventional tablet, as the ingredients of the tablet were released in the intestine at a concentration which was too high. These side effects were evident with Fumaderm , which due to high concentration of drug release in the stomach, was known to cause undesirable side effects like nausea, vomiting, abdominal cramps, headache, dizziness and flushing (Antonie et al, Indian Journal of Dermatology, Venereology and Leprology, Vol. 73, No. 2, March-April, 2007, pp. 133-137)

An improved capsule formulation of dimethyl fumarate was approved by USFDA in 2013, under the tradename Tecfidera® (Biogen Idec, Inc) for the treatment of multiple sclerosis. Tecfidera® comprises enteric-coated micro-tablets in capsules, wherein it is theorized that the micro-tablets are incrementally released by the stomach and passed into the small intestine and the active ingredients are released in smaller dosages, thus avoiding the gastrointestinal irritations and side effects. (See U.S. Pat. No. 7,320,999). Tecfidera® is used in Multiple sclerosis patients at a starting dose of 120 mg twice a day. After 7 days, the dose is increased to the maintenance dose of 240 mg twice a day. The product, however, has also been reported to cause the adverse events associated with flushing and gastrointestinal side effects such as diarrhea, abdominal pain, nausea, flatulence etc. (Phillips et al., Multiple Sclerosis and Related Disorders (2014) 3, 513-519). It is further known to show high variability in pharmacokinetic profiles (Sheikh et al., Clinical Therapeutics, 2013, Vol. 35, NO. 10, 1583-1594). Another approach for reducing the side effects associated with dimethyl fumarate, contemplated in the art is through use of controlled release formulations as disclosed in US20090304790 and WO2015028472.

Orally administered dimethyl fumarate is prone to pre-systemic metabolism by esterases associated with the intestinal lumen and the mucosa which is responsible for the rapid disappearance of the drug from the absorption site. The approved label of Tecfidera® suggests rapid presystemic hydrolysis of dimethyl fumarate to its active metabolite, monomethyl fumarate (MMF) and that dimethyl fumarate is not quantifiable in plasma. Werdenberg et al. also discloses complete biotransformation of dimethyl fumarate to MMF, before reaching the liver (Werdenberg et al., Biopharm. Drug Dispos. 2003, 24: 259-273).

The present invention is a novel improved pharmaceutical composition of dimethyl fumarate which addresses these drawbacks. Unlike the prior art approach of making a controlled release formulation, the present inventors have formulated a delayed release composition which exhibits increased bioavailability as compared to Tecfidera® when administered at same dose under similar conditions. The term "increased bioavailability" is intended to mean that the composition of the present invention requires a lower dose to equivalent blood levels of the active metabolite, monomethyl fumarate compared to that of Tecfidera® capsules. Further the term "dose" refers to the amount of dimethyl fumarate in the composition in the form of a capsule. The capsules are given twice daily and therefore the "daily dose" is the amount of dimethyl fumarate in two capsules.

SUMMARY OF THE INVENTION

The present invention provides an oral pharmaceutical composition comprising dimethyl fumarate and a pharmaceutically acceptable agent that inhibits the enzyme catalyzed degradation of dimethyl fumarate, said composition when compared to a composition devoid of the agent provides an increased bioavailability in humans such that the dose of dimethyl fumarate is reduced.

The present invention further provides a method of increasing the bioavailability of dimethyl fumarate, the method comprising orally administering a pharmaceutical composition comprising dimethyl fumarate and a pharmaceutically acceptable agent that inhibits the enzyme catalyzed degradation of dimethyl fumarate.

According to a further aspect of the present invention, there is provided an oral pharmaceutical composition as disclosed herein for use in the treatment of autoimmune disorders such as multiple sclerosis, psoriasis, psoriatic arthritis, neurodermatitis, inflammatory bowel disease, such as Crohn's disease and ulcerative colitis, polyarthritis, rheumatoid arthritis, lupus nephritis and myasthenia gravis. There is also provided an oral pharmaceutical composition as disclosed herein for use in preventing or reducing the risk of organ transplantation rejection.

DETAILED DESCRIPTION OF THE INVENTION

The present invention provides an improved pharmaceutical composition of dimethyl fumarate comprising dimethyl fumarate and a pharmaceutically acceptable agent that inhibits the enzyme catalyzed degradation of dimethyl fumarate. The present inventors have surprisingly found that a pharmaceutical composition comprising dimethyl fumarate and a pharmaceutically acceptable agent that inhibits the enzyme catalyzed degradation of dimethyl fumarate, increases the oral bioavailability of dimethyl fumarate as compared to the composition devoid of such agent. Accordingly, a lower dose of pharmaceutical composition of the invention achieves the same therapeutic effect in a subject when compared to the therapeutic dose of Tecfidera®.

Particularly, the present invention provides an oral pharmaceutical composition comprising dimethyl fumarate and a pharmaceutically acceptable agent that inhibits the enzyme catalyzed degradation of dimethyl fumarate, said composition when compared to a composition devoid of the agent provides an increased bioavailability in humans such that the dose of dimethyl fumarate is reduced by atleast about 10%. That is to mean, the dose at which the present composition would achieve similar blood levels as compared to 240 mg Tecfidera® is 10% lower than Tecfidera® dose. More particularly, the composition of the present invention leads to reduction of dosage in the range of from about 10% to 20%. In a specific embodiment, the dose is reduced by in the range of 14 to 16%. In yet another specific embodiment, the dose is reduced by about 15%.

In another aspect, the invention provides a method of increasing the oral bioavailability of dimethyl fumarate, the method comprising orally administering an oral pharmaceutical composition comprising dimethyl fumarate and a pharmaceutically acceptable agent that inhibits the enzyme catalyzed degradation of dimethyl fumarate.

The "pharmaceutically acceptable agent" herein refers to an agent that inhibits the enzyme catalyzed degradation of dimethyl fumarate. The agent may be an inhibitor of esterase enzyme responsible for the hydrolysis of dimethyl fumarate to monomethylfumarate. One or more agents that inhibit the enzyme catalyzed degradation of dimethyl fumarate may be included in the composition. Examples of such inhibitors include, but are not limited to, an alkyl or aryl esters of acids such as acetic, propionic, valeric, butyric, pivalic, benzoic and the like for example ethyl acetate, phenyl propionate, naphthyl valerate, methyl butyrate; also polyol esters such as glycerol esters for example glyceryl tributyrate; or alkyl or aryl esters of an amino acid or a small peptide or a derivative thereof, including $\beta$-aryl-$\beta$-aminoacids thereof. For example aspartyl-phenylalanine methyl ester (aspartame), ethyl esters of $\beta$-phenyl-$\beta$-alanine, $\beta$-(3-nitrophenyl)-$\beta$-alanine, and $\beta$-amino-$\beta$-piperonylpropionic acid, and of monoethyl $\beta$-amino-$\beta$-piperonylisocuccinate and the like. Preferably, the pharmaceutically acceptable agent is aspartame.

The pharmaceutical agent that inhibits the enzyme catalyzed degradation of dimethyl fumarate may be used in amounts in the range from 5% to 20% of the weight of dimethyl fumarate. In a preferred embodiment, the pharmaceutically agent is used in amounts in the range of about 10% to 15% of weight of dimethyl fumarate. When more than one pharmaceutically acceptable agent is used in the composition, the above ranges of amounts reflect the total amount of such agents that may be used in the composition. In a preferred embodiment, the pharmaceutically acceptable agent is aspartame which is used in an amount in the range of about 10% to about 15% of the weight of dimethyl fumarate.

The pharmaceutical composition of present invention may further comprise an 'alkalizer'. Examples of alkalizer include, but are not limited to calcium carbonate, disodium hydrogen phosphate, trisodium orthophosphate, sodium hydroxide, sodium carbonate, potassium hydroxide, sodium bicarbonate, dipotasium carbonate, tromethamine, aluminum trihydroxide, magnesium dihydroxide, aluminium oxide, magnesium oxide or mixture thereof. Preferably, the alkalizer is magnesium oxide. One or more alkalizers may be included in the composition.

The alkaliser may be used in amounts in the range of 0.1% to 10% of the total weight of the composition. In a preferred aspect, the alkalizer may be used in the range of about 2% to 8% of the total weight of the composition. In a particularly preferred aspect, the amount of alkalizer may be about 6% of the total weight of the composition.

The pharmaceutical composition of present invention is in the form of delayed release composition. The delayed release composition of the present invention shows immediate release profile in intestinal pH, such that the pharmaceutical composition of the present invention when tested for dissolution in a USP Apparatus II at 100 rpm in 500 ml of 0.1N HCl for 2 hours followed by a change to pH 6.8 buffer, exhibits the following dissolution profile.

a) 5% or less of total dimethyl fumarate is released in 2 hours
b) in the range of 50%-80% of total dimethyl fumarate is released in 10 minutes or less in pH 6.8
c) in the range of 80%-100% of total dimethyl fumarate is released in between 15 minutes to 60 minutes in pH 6.8

In a preferred aspect, the oral pharmaceutical composition of the present invention is in the form of a capsule. Preferably, the pharmaceutical composition comprises minitablets filled into a capsule shell. In a further preferred aspect, each minitablet is coated with a delayed release coating so as to prevent release of dimethyl fumarate into stomach. In an aspect, each minitablet has a core and a coat. The core comprises dimethyl fumarate and a pharmaceutically acceptable agent that prevents the enzyme catalyzed degradation of dimethyl fumarate. The coating comprises a polymer for preventing the release of dimethyl fumarate, The capsules may be filled with the required number of minitablet so as to comprise a single dosage unit. For example, for a capsule comprising 240 mg dimethyl fumarate, with each minitablet having about 6 mg of dimethyl fumarate, a total of 40 minitablets would be required to be filled in the capsule shell. In preferred example, the pharmaceutical composition of the present invention comprises dimethyl fumarate in an amount from about 195 to 215 mg/capsule and 4.3 to 8.6 mg/minitablet.

The core of minitablets according to the present composition may further comprise pharmaceutically acceptable excipients and additives selected from the group comprising diluents or fillers, binders, disintegrants, stabilizers, glidants, lubricants, surfactants, solubilizing agents, anti-adherants, buffers, wetting agents, emulsifying agents, preservatives, coloring agents and sweetener. Examples of fillers useful in the present invention include but are not limited to silicified microcrystalline cellulose, microcrystalline cellulose, lactose, pregelatinized starch, dry starch, mannitol, sodium chloride, compressible sugar, sorbitol, xylitol, mannose, dextrose or combinations thereof. Examples of disintegrants useful in the present invention include but are not limited to croscarmellose sodium, sodium starch glycolate, povidone, crospovidone or combinations thereof. Examples of glidants useful in the present invention include but are not limited to colloidal silicon dioxide, talc, magnesium stearate, precipitated silicon dioxide, fumed silicon dioxide, glyceryl monostearate or combinations thereof. Examples of lubricants useful in the present invention include but are not limited to talc, magnesium stearate, calcium stearate, glyceryl behenate, glyceryl monostearate, mineral oil, sodium lauryl sulfate, zinc stearate or combinations thereof. The above stated pharmaceutical composition may be prepared by conventional methods known in the art for preparing pharmaceutical compositions and dosage forms. As an illustration, the method of of preparation comprises combining about 30% w/w to about 80% w/w of dimethyl fumarate, about 3.5% w/w to about 55% w/w of one or more fillers, about 0.1% w/w to about 20% w/w of one or more disintegrant, about 0.1% w/w to about 5.0% w/w of one or more glidant, about 0.1% w/w to about 10.0% w/w of one or more lubricants, about 1% w/w to about 20% w/w of one or more pharmaceutically acceptable agent that inhibits the enzyme catalyzed degradation of dimethyl fumarate (dimethyl fumarate). The amounts of such excipients and additives may be adjusted such that the properties of the pharmaceutical composition are not deteriorated.

The delayed release coating polymer useful in the present invention include but are not limited to methacrylic acid copolymers like Eudragit L 100 (methacrylic acid-methyl methacrylate copolymer 1:1), Eudragit L30D 55 (methacrylic acid-ethyl acrylate copolymer 1:1, 30% dispersion), polyacrylamides, phthalate derivatives such as acid phthalates of carbohydrates, amylose acetate phthalate, hydroxypropylmethylcellulose phthalate, methylcellulose phthalate, cellulose acetate phthalate, other cellulose ester phthalates, cellulose ether phthalates, hydroxypropylcellulose phthalate, hydroxypropylethylcellulose phthalate polyvinyl acetate phthalate, poly acrylic, shellac and vinyl acetate and crotonic acid copolymers, etc. The delayed release coating may be in the form of a two part coating. The coating may further include a plasticizer. Examples of plasticizers useful in the present invention include but are not limited to Triethylcitrate, acetyl-triethylcitrate, tributylcitrate, acetyl-tributylcitrate, tricetin, diethylphthalate, dibiutysebacate, dibutylphthlate, polyethylengycole, glycerole, and polysorbate or combinations thereof. The composition may comprise, dimethyl fumarate in an amount in the range of about 195 mg to about 215 mg, more particularly in the range from about 200 mg to 210 mg in a single dosage unit. In a preferred aspect, each single dosage unit may comprise about 204 mg of dimethyl fumarate.

According to one aspect of the present invention there is provided an oral pharmaceutical composition comprising dimethyl fumarate in the range of about 195 mg to about 215 mg, more particularly in the range from about 200 mg to about 210 mg, and one or more agent which inhibits the enzyme catalyzed degradation of dimethyl fumarate in an amout sufficient to increase the bioavailability of dimethyl fumarate. Preferably the agent is aspartame and is used in the composition in an amount from about 20 mg to about 30 mg. The said composition in the form of a capsule comprising mini tablets wherein each minitablet is coated with at least one delayed release coating.

According to another aspect of the present invention there is provided a method of increasing bioavailability comprising orally administering a pharmaceutical composition comprising dimethyl fumarate and a pharmaceutically acceptable agent that inhibits the enzyme catalyzed degradation of dimethyl fumarate. The pharmaceutically acceptable agent that may be used according to the invention are as defined hereinabove. In a preferred aspect, the pharmaceutically acceptable agent is aspartame. In a particularly preferred aspect, the amount of aspartame is in the range of about 10% to about 15% of the weight of dimethyl fumarate. In yet another aspect of the invention, the method comprises using a pharmaceutical composition further comprising an alkalizer.

In yet another preferred aspect, the method comprises administering an oral pharmaceutical composition comprising dimethyl fumarate in the range of about 195 mg to about 215 mg, more particularly in the range from about 200 mg to about 210 mg, more particularly 204 mg of dimethyl fumarate, and one or more agent which inhibits the enzyme catalyzed degradation of dimethyl fumarate in an amount sufficient to increase the bioavailability of dimethyl fumarate. Preferably the agent is aspartame and used in the composition in an amount from about 20 mg to about 30 mg. The said composition in the form of a capsule comprising mini tablets wherein each minitablet is coated with at least one delayed release coating. In preferred example, the method comprises administering orally, a pharmaceutical composition of the present invention comprising dimethyl fumarate in an amount from about 195 to 215 mg/capsule and 4.3 to 8.6 mg/minitablet.

The pharmaceutical composition of present invention may be useful for treating autoimmune disorders like multiple sclerosis, psoriasis, psoriatic arthritis, neurodermatitis, inflammatory bowel disease, such as Crohn's disease and ulcerative colitis, polyarthritis, rheumatoid arthritis, lupus nephritis, myasthenia gravis etc. The composition may also be useful in organ transplantation (prevention of rejection). Advantageously, the compositions of the present invention are useful in treatment of Multiple Sclerosis with lower side effects like gastro-intestinal side effects, flushing etc. as compared to Tecfidera®.

The pharmaceutical composition of the present invention is adapted to be administered at a dose of at least 10% lower than the dose of Tecfidera®. In a preferred aspect, the dose is in the range of about 10 to 20% lower than Tecfidera®. In a specific embodiment, the dose is reduced by 14 to 16% of the dose of Tecfidera®. In yet another specific embodiment, the dose is reduced by 15% of the dose of Tecfidera®. The pharmaceutical composition may be administered twice daily in an amount as appropriate daily doses for treatment of particular disease. For example, daily dose of dimethyl fumarate for the treatment of multiple sclerosis may range from 390 mg to 430 mg given given orally in a twice daily regimen in the form of the composition of the invention comprising dimethyl fumarate in the range of about 195 mg to about 215 mg, more particularly in the range from about 200 mg to about 210 mg.

EXAMPLES

The compositions of the present invention example are illustrated as examples below. However, it is to be noted that the present disclosure is not limited to the illustrative examples but can be realized in various other ways.

Example 1

Preparation of Pharmaceutical Composition of Dimethyl Fumarate 204 mg a) Preparation of Core of minitablets—Silicified Microcrystalline Cellulose, Magnesium Oxide and Aspartame (25 mg), Dimethyl Fumarate (204 mg), Croscarmellose Sodium and Colloidal Silicon Dioxide were sifted were sifted through ASTM #40 sieve and then loaded in suitable blender and mixed for 45 minutes at suitable rpm. Sifted Talc (sifted through ASTM #40) was then and magnesium stearate (sifted through ASTM 60#) was transferred to this blender and further mixed for 5 minutes. It was then compressed in a suitable compression machine at target weight of 13 mg per core of minitablet.

b) Delayed Release Coating-I—Methacrylic Acid Co-polymer Type A (Eudragit L 100) was added to a mixture of Isopropyl Alcohol and Purified Water under stirring Once the solution gets clear Triethyl Citrate is added under stirring and continued stirring for 30 minutes to form delayed release coating solution. The cores were coated using delayed release coating solution in 36 inch perforated coating pan and dried.

c) Delayed Release Coating-II—Methacrylic acid-Ethyl acrylate Copolymer 1:1, 30% Dispersion (Eudragit L30D 55) was filtered through ASTM 100# sieve and transfered to suitable stainless steel tank. Triethyl citrate was added under stirring. Purified water was divided into two parts. The part quantity of purified water was added under stirring for 15 min. Simethicone emulsion and talc was added under stirring. Remaining purified water was added stirring continued at slow speed for further 30 minutes or till uniform delayed release coating dispersion-II is obtained. The delayed release coated minitablet were loaded in perforated coating pan. The coated minitablets were further coated using delayed release coating dispersion-II in 36 inch perforated coating pan and dried.

d) Capsule Filling—Empty hard gelatin capsule shells were filled with Dimethyl Fumarate Delayed Release minitablets were filled at required weight of mini tablets per capsule shell. Each capsule may be filled with 25 minitablets, each minitablets comprising about 8.1 mg of dimethylfumarate for a single dosage unit comprising 204 mg of dimethyl fumarate.

Example 2

Dissolution Profile of Dimethyl Fumarate Capsules 204 mg of Example 1

For dissolution testing a 204 mg capsule of dimethyl fumarate of Example 1 is placed in USP Apparatus II in a 500 mL of 0.1N HCl at 100 RPM for 2 hours followed by a change in media to buffer of pH 6.8. Similarly, the 240 mg Tacfidera® capsule was tested for dissolution. For specified time periods fractions are collected and analyzed for dimethyl fumarate. The percentage dissolution at each time point is calculated. The dissolution profiles at 0.1N HCl and pH 6.8 are as shown in Table 1.

TABLE 1

Dissolution Profile of composition of Example 1 and Tecfidera ®

| Time | dimethyl fumarate Capsules 204 mg, Of Example 1 | Tecfidera ® 240 mg, |
|---|---|---|
| 0.1N HCl | | |
| 120 minutes | 0 | 0 |
| pH 6.8 | | |
| 10 minutes | 75 | 97 |
| 15 minutes | 90 | Nd* |
| 20 minutes | Nd* | 98 |
| 30 minutes | 96 | 97 |
| 45 minutes | 94 | 97 |
| 60 minutes | 93 | 96 |

*Not determined

This example illustrates that the composition of the present invention is not a controlled release composition, rather it is a delayed release composition i.e. it does not release the drug in the acidic fluids in the stomach but once the composition in the form of a minitablet is emptied from the stomach into the intestine the enteric coat dissolves and the drug is at once released. Minitablets are emptied into the intestine unit by unit and so for this example not all of the 204 mg of dimethyl fumarate is at once released rather only 8.1 mg dimethyl fumarate in the minitablet is released at a particular time the enteric coat on the minitablet dissolves.

Example 3

Variations of the composition of Example 1 were made with dimethyl fumarate varying in the range from 195 to 215 mg/capsule and 4.3 to 8.6 mg/minitablet.

Example 4

A Study to determine the relative bioavailability of Dimethyl Fumarate 204 mg Delayed Release Capsules of Example 1 Vs. Tecfidera® 240 mg Delayed Release Capsules of Biogen Idec Inc., was performed in healthy adult subjects. After a supervised overnight fast for at least 10 hours, subjects swallowed single oral dose (1×240 mg Tecfidera® or 1×204 mg Delayed Release Capsule of Example 1) with about 240 mL of water at ambient temperature in the morning according to the randomization schedule. There was a washout period of Eight (8) Days between each dosing. In each of the two study periods, 21 blood samples were collected including pre-dose blood sample. A pre-dose blood sample of 5 mL was collected within 1 hour prior to schedule dosing. Post-dose blood samples (5 mL each) were collected at regular time interval during 10 hour period and analysed for the metabolite, monomethyl fumarate, using a validated LC/MS/MS method and Cmax, Tmax, $T_{1/2}$ and AUC determined. It was observed that the 204 mg delayed release capsule of example 1 showed comparable Cmax, Tmax, $AUC_{0-t}$ and $AUC_{0-\infty}$ to 240 mg of Tecfidera® capsule. (Table 2).

TABLE 2

Pharmacokinetic data from monomethyl fumarate concentrations in plasma

| | $AUC_{0-t}$ (hr · mg/L) | $AUC_{0-\infty}$ (hr · mg/L) | $C_{max}$ (mg/L) | $T_{max}$ (hr) | $T_{1/2}$ (hr) |
|---|---|---|---|---|---|
| Example 1 (Mean) | 3.2 (n = 18) | 3.2 (n = 18) | 2.3 (n = 18) | 2.25 (n = 18) | 0.64 (n = 18) |
| Tecfidera ® 240 mg | 3.4 (n = 18) | 3.3 (n = 17) | 2.2 (n = 18) | 2.63 (n = 18) | 0.64 (n = 17) |

The invention claimed is:

1. An oral pharmaceutical composition comprising minitablets filled in a capsule, each minitablet comprising a core comprising dimethyl fumarate and aspartame, and an enteric coating, wherein the oral pharmaceutical composition does not release dimethyl fumarate in acidic fluids in a stomach but once a minitablet is emptied from the stomach into an intestine the enteric coating dissolves and the dimethyl fumarate and the aspartame are released, said composition provides an increased bioavailability in humans such that the dose of dimethyl fumarate is reduced by about 10% to about 20%, when compared to a composition devoid of the aspartame.

2. An oral pharmaceutical composition as in claim 1, wherein the core further comprises an alkalizer.

3. An oral pharmaceutical composition as in claim 1, wherein the amount of aspartame is in the range of about 10% to about 15% of the weight of dimethyl fumarate.

4. An oral pharmaceutical composition as in claim 1, wherein the composition comprises dimethyl fumarate in an amount from 195 to 215 mg/capsule and 4.3 to 8.6 mg/minitablet.

5. An oral pharmaceutical composition as in claim 1, wherein the composition comprises 204 mg of dimethyl fumarate.

6. A method of increasing the bioavailability of dimethyl fumarate the method comprising orally administering the oral pharmaceutical composition of claim 1.

7. A method as in claim 6, wherein the core further comprises an alkalizer.

8. A method as in claim 6, wherein the amount of aspartame is in the range of about 10% to about 15% of the weight of dimethyl fumarate.

9. A method as in claim 6, wherein the composition comprises dimethyl fumarate in an amount from 195 mg to 215 mg/capsule and 4.3 to 8.6 mg/minitablet.

10. A method as in claim 6, wherein the composition comprises 204 mg of dimethyl fumarate.

* * * * *